(12) United States Patent
Schaffer et al.

(10) Patent No.: US 7,625,570 B1
(45) Date of Patent: Dec. 1, 2009

(54) METHODS FOR PURIFYING ADENO-ASSOCIATED VIRUS

(75) Inventors: David V. Schaffer, Pleasant Hill, CA (US); Joshua N. Leonard, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/372,552

(22) Filed: Mar. 9, 2006

Related U.S. Application Data

(60) Provisional application No. 60/661,161, filed on Mar. 10, 2005.

(51) Int. Cl.
*A61K 39/23* (2006.01)
*C07K 2/00* (2006.01)

(52) U.S. Cl. .............. 424/233.1; 424/204.1; 424/184.1; 514/2

(58) Field of Classification Search .............. 424/233.1, 424/204.1, 184.1; 514/2
See application file for complete search history.

(56) References Cited

U.S. PATENT DOCUMENTS 6,143,548 A * 11/2000 O'Riordan et al. .......... 435/239
7,056,723 B2 * 6/2006 Heller et al. ................ 435/239

OTHER PUBLICATIONS

Leonard et al., Enhanced Preparation of Adeno-Associated Viral Vectors by Using High Hydrostatic Pressure to Selectively Inactivate Helper Adenovirus, Biotechnology and Bioengineering, vol. 97, No. 5, Aug. 1, 2007, pp. 1170-1179.*
Pontes L, F.L., Giongo V, Araujo JRV, Sepulveda A, Vilas-Boas M, Bonafe CFS, Silva JL, *Pressure inactivation of animal viruses: potential biotechnological applications*, in *High Pressure Research in the Biosciences and Biotechnology*, H. K, Editor. 1997, Leuven University Press.
Wilkinson N, Kurdziel AS, Langton S, Needs S, Cook N. Resistance of poliovirus to inactivation by high hydrostatic pressures. Innovative Food Science and Emerging Technologies. 2001. 2:95-98.

* cited by examiner

*Primary Examiner*—T. D. Wessendorf
(74) *Attorney, Agent, or Firm*—Paula A. Borden; Bozicevic, Field & Francis LLP

(57) ABSTRACT

The present invention provides methods of purifying adeno-associated virus (AAV) from compositions comprising AAV and at least a second, non-AAV; and methods for selectively inactivating a non-adeno-associated virus (non-AAV) in a liquid composition comprising AAV and the non-AAV. The methods generally involve subjecting the composition to hydrostatic pressure such that the non-AAV is selectively inactivated.

19 Claims, No Drawings

METHODS FOR PURIFYING ADENO-ASSOCIATED VIRUS

CROSS-REFERENCE

This application claims the benefit of U.S. Provisional Patent Application No. 60/661,161, filed Mar. 10, 2005, which application is incorporated herein by reference in its entirety.

STATEMENT REGARDING FEDERALLY SPONSORED RESEARCH

The U.S. government may have certain rights in this invention, pursuant to grant no. EB003007 awarded by the National Institutes of Health.

FIELD OF THE INVENTION

This application is in the field of inactivation of viruses and purification of viruses, particularly adeno-associated viruses.

BACKGROUND OF THE INVENTION

Recombinant adeno-associated virus (AAV) is a highly promising gene therapy vector for numerous reasons, including its non-pathogenicity and its ability to induce long-term expression of a transgene in multiple target cell types. However, the large scale production of AAV is complex, either involving transient plasmid transfection or co-infection with a helper virus (such as adenovirus), which must eventually be removed from the product to avoid helper-induced pathogenicity. The helper adenovirus approach offers some advantages for large scale production; however, adenovirus must then be eliminated during AAV purification. One widely used procedure for inactivating adenovirus following the production phase involves heating to 55° C. However, this procedure results in the concomitant loss of ~50% of the active AAV particles.

There is a need in the art for alternative, rapid, robust, and economical methods that selectively inactivate undesired viruses while leaving AAV particles intact. The present invention addresses this need.

LITERATURE

Pontes L, F. L., Giongo V, Araujo J R V, Sepulveda A, Vilas-Boas M, Bonafe C F S, Silva J L, *Pressure inactivation of animal viruses: potential biotechnological applications*, in *High Pressure Research in the Biosciences and Biotechnology*, H. K, Editor. 1997, Leuven University Press: Leuven. p. 91-94; Wilkinson N, Kurdziel A S, Langton S, Needs S, Cook N. Resistance of poliovirus to inactivation by high hydrostatic pressures. Innovative Food Science and Emerging Technologies. 2001. 2:95-98;

SUMMARY OF THE INVENTION

The present invention provides methods of purifying adeno-associated virus (AAV) from compositions comprising AAV and at least a second, non-AAV; and methods for selectively inactivating a non-adeno-associated virus (non-AAV) in a liquid composition comprising AAV and the non-AAV. The methods generally involve subjecting the composition to hydrostatic pressure such that the non-AAV is selectively inactivated.

DEFINITIONS

"AAV" is an abbreviation for adeno-associated virus, and may be used to refer to the virus itself or derivatives thereof. The term covers all subtypes and both naturally occurring and recombinant forms, except where required otherwise. The abbreviation "rAAV" refers to recombinant adeno-associated virus, also referred to as a recombinant AAV vector (or "rAAV vector"). The term "AAV" includes AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), avian AAV, bovine AAV, canine AAV, equine AAV, primate AAV, non-primate AAV, and ovine AAV. "Primate AAV" refers to AAV that infect primates, "non-primate AAV" refers to AAV that infect non-primate mammals, "bovine AAV" refers to AAV that infect bovine mammals, etc.

An "rAAV vector" as used herein refers to an AAV vector comprising a polynucleotide sequence not of AAV origin (i.e., a polynucleotide heterologous to AAV), typically a sequence of interest for the genetic transformation of a cell. In general, the heterologous polynucleotide is flanked by at least one, and generally by two AAV inverted terminal repeat sequences (ITRs). The term rAAV vector encompasses both rAAV vector particles and rAAV vector plasmids.

An "AAV virus" or "AAV viral particle" or "rAAV vector particle" refers to a viral particle composed of at least one AAV capsid protein (typically by all of the capsid proteins of a wild-type AAV) and an encapsidated polynucleotide rAAV vector. If the particle comprises a heterologous polynucleotide (i.e. a polynucleotide other than a wild-type AAV genome such as a transgene to be delivered to a mammalian cell), it is typically referred to as an "rAAV vector particle" or simply an "rAAV vector". Thus, production of rAAV particle necessarily includes production of rAAV vector, as such a vector is contained within an rAAV particle.

A "helper virus" for AAV refers to a virus that allows AAV (e.g. wild-type AAV) to be replicated and packaged by a mammalian cell. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

An "infectious" virus or viral particle is one that comprises a polynucleotide component which it is capable of delivering into a cell for which the viral species is trophic. The term does not necessarily imply any replication capacity of the virus. Assays for counting infectious viral particles are described elsewhere in this disclosure and in the art. Viral infectivity can be expressed as the P:I ratio, or the ratio of total viral particles to infective viral particles.

A "replication-competent" virus (e.g. a replication-competent AAV) refers to a phenotypically wild-type virus that is infectious, and is also capable of being replicated in an infected cell (i.e. in the presence of a helper virus or helper virus functions). In the case of AAV, replication competence generally requires the presence of functional AAV packaging genes. In general, rAAV vectors as described herein are replication-incompetent in mammalian cells (especially in human cells) by virtue of the lack of one or more AAV packaging genes. Typically, such rAAV vectors lack any AAV packaging gene sequences in order to minimize the possibility that replication competent AAV are generated by recombination between AAV packaging genes and an incoming rAAV vector. In many embodiments, rAAV vector preparations as described herein are those which contain few if any replication competent AAV (rcAAV, also referred to as RCA) (e.g., less than about 1 rcAAV per $10^2$ rAAV particles, less than about 1 rcAAV per $10^4$ rAAV particles, less than about 1 rcAAV per $10^8$ rAAV particles, less than about 1 rcAAV per $10^{12}$ rAAV particles, or no rcAAV).

"Recombinant," as applied to a polynucleotide means that the polynucleotide is the product of various combinations of cloning, restriction or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

As used herein, "pharmaceutically acceptable carrier" includes any material which, when combined with an active ingredient of a composition, allows the ingredient to retain biological activity and without causing disruptive physiological reactions, e.g., disruptive reactions with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well known conventional methods (see, for example, Remington's Pharmaceutical Sciences, Chapter 43, 14th Ed. or latest edition, Mack Publishing Co., Easton Pa. 18042, USA; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a viral composition" includes a plurality of such compositions and reference to "the hydrostatic pressure treatment" includes reference to one or more hydrostatic pressure treatments and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides methods of purifying adeno-associated virus (AAV) from compositions comprising AAV and at least a second, non-AAV; and methods for selectively inactivating a non-adeno-associated virus (non-AAV) in a liquid composition comprising AAV and the non-AAV. The methods generally involve subjecting the composition to hydrostatic pressure such that the non-AAV is selectively inactivated.

The methods are useful for generating compositions that comprise active (infectious) AAV (e.g., AAV particles), e.g., recombinant AAV (rAAV), but do not include active (infectious) non-AAV virus (e.g., non-AAV viral particles) present in the composition before the hydrostatic pressure treatment. For convenience, the viral composition before being treated with a subject method is referred to herein as the "starting composition" or the "untreated composition"; and the viral composition after being treated with a subject method is referred to herein as the "treated composition" or the "hydrostatic pressure-treated composition." Exemplary, non-limiting rAAV particles include heterologous nucleic acids such as are discussed in, e.g., WO 2005/005610.

The subject methods involve subjecting a composition comprising an AAV (including an rAAV) and a non-AAV virus to high hydrostatic pressure. The non-AAV virus will in many embodiments be a helper virus. Helper viruses include, but are not limited to, adenoviruses, e.g., Adenovirus type 5 of subgroup C, e.g., serotypes 1, 2, 4, 6, and 7; herpesviruses, e.g., herpes simplex viruses, Epstein-Barr viruses, cytomegaloviruses, and pseudorabies viruses; and poxviruses such as vaccinia. In some embodiments, the helper virus is adenovirus type 5 (Ad5). In some embodiments, the helper virus is a temperature-sensitive Ad5.

A subject method results in selective inactivation of the non-AAV virus present in the untreated composition. In some embodiments, inactivation of the non-AAV virus results in or is manifested by a reduction in the infectivity of the non-AAV virus. An "infectious" virus or viral particle is one that comprises a polynucleotide component which it is capable of delivering into a cell for which the viral species is trophic. Viral infectivity can be expressed as the P:I ratio, or the ratio of total viral particles to infective viral particles. Infectivity is determined using standard assay methods. For example, cells (e.g., primary cells, cells of a cell line, etc.) that are permissive for the non-AAV virus is contacted with the treated composition, and the number of infected cells is determined, and compared with the number of infected cells when the same cells are contacted with the untreated composition.

A subject method reduces the infectivity of the non-AAV virus present in the untreated composition by at least about 50%, at least about 60%, at least about 70%, at least about 80%, at least about 90%, at least about 95%, at least about 98%, or at least about 99%, or 100%. Thus, e.g., less than about 50%, less than about 40%, less than about 30%, less than about 25%, less than about 20%, less than about 15%, less than about 10%, less than about 5%, less than about 2%, or less than about 1% of the non-AAV virus present in the treated composition are infectious. In some embodiments, a subject method results in substantially no infectious non-AAV virus in the treated composition, e.g., the number of infectious non-AAV virus, if any, in the treated composition is undetectable using a standard method for assessing infectivity.

In some embodiments, inactivation of the non-AAV virus results in or is manifested by a reduction in a reduction in an immune response in a mammalian subject to the non-AAV virus (e.g., non-AAV virus protein(s)). In these embodiments, a subject method results in a treated viral composition that does not substantially elicit an immune response to the non-AAV virus (e.g., non-AAV virus protein(s)) in a mammalian host. Thus, e.g., a treated viral composition, if it elicits any detectable immune response at all to the non-AAV virus (e.g., non-AAV virus protein(s) in a mammalian host, elicits an immune response that is reduced by at least about 50%, at least about 60%, at least about 70%, at least about 80%, or at least about 90%, or more, compared to the immune response of a mammalian host to the non-AAV virus (e.g., non-AAV virus protein(s).

A subject method selectively inactivates the non-AAV virus present in the untreated composition, e.g., a subject method does not substantially inactivate (reduce the infectivity of) the AAV present in the viral composition. At least about 70%, at least about 80%, at least about 85%, at least about 90%, at least about 95%, at least about 98%, or more, of the AAV present in the untreated composition remain infectious following treatment with a subject method. Thus, e.g., infectivity of the AAV present in the untreated composition is reduced by less than about 30%, less than about 25%, less than about 20%, less than about 15%, less than about 10%, less than about 5%, or less than about 2%.

Infectivity of the AAV is readily determined using standard assays. As one non-limiting example, 293 cells can be contacted in vitro with the treated composition, where the untreated composition comprises an rAAV that comprises a nucleotide sequence encoding a protein that provides a detectable signal (e.g., a fluorescent protein such as a green fluorescent protein); and the number of 293 cells that become positive for the detectable signal is compared to the number of 293 cells that become positive for the signal when contacted with the untreated composition. Examples of methods for determining infectivity of AAV are also discussed in U.S. Pat. Nos. 5,658,776 and 6,642,051.

A subject method involves subjecting a viral composition comprising an AAV and a non-AAV virus to a hydrostatic pressure at a pressure and for a time such that the non-AAV virus is selectively inactivated. In some embodiments, composition is subjected to a pressure in a range of from about 200 MPa to about 1000 MPa, e.g., in a range of from about 200 MPa to about 250 MPa, from about 250 MPa to about 300 MPa, from about 300 MPa to about 350 MPa, from about 350 MPa to about 400 MPa, from about 400 MPa to about 450 MPa, from about 450 MPa to about 500 MPa, from about 500 MPa to about 600 MPa, from about 600 MPa to about 700 MPa, from about 700 MPa to about 800 MPa, from about 800 MPa to about 900 MPa, or from about 900 MPa to about 1000 Mpa, for a time such that the non-AAV virus is selectively inactivated.

Suitable time periods for achieving selective inactivation of the non-AAV virus present in the viral composition range from about 1 minute to about 3 hours, e.g., from about 1 minute to about 5 minutes, from about 5 minutes to about 10 minutes, from about 10 minutes to about 15 minutes, from about 15 minutes to about 20 minutes, from about 20 minutes to about 30 minutes, from about 30 minutes to about 45 minutes, from about 45 minutes to about 60 minutes, from about 60 minutes to about 90 minutes, from about 90 minutes to about 120 minutes, or from about 120 minutes to about 180 minutes.

In many embodiments, the temperature of composition is held relatively constant during treatment with hydrostatic pressure, e.g., the temperature of the composition does not fluctuate by more than about 1° C., by more than about 2° C., by more than about 3° C., by more than about 4° C., or by more than about 5° C. In some embodiments, the temperature of the composition is held at or below about 40° C., e.g., the temperature of the composition is maintained at a relatively constant temperature in the range of from about 4° C. to about 40° C., e.g., from about 4° C. to about 5° C., from about 5° C. to about 7° C., from about 7° C. to about 10° C., from about 10° C. to about 15° C., from about 15° C. to about 20° C., from about 20° C. to about 25° C., from about 25° C. to about 30° C., from about 30° C. to about 35° C., or from about 35° C. to about 40° C.

In general, the higher the hydrostatic pressure with which the viral composition is treated, the shorter the time required to selectively inactivate the non-AAV virus present in the viral composition. The following are exemplary, non-limiting embodiments of the subject treatment method.

In some embodiments, a viral composition is subjected to a pressure in a range of from about 200 MPa to about 500 MPa for a time such that the non-AAV virus is selectively inactivated. In some of these embodiments, the viral composition is subjected to a pressure in a range of from about 200 MPa to about 500 MPa for a time period of from about 1 minute to about 3 hours. In some embodiments, the viral composition is subjected to a pressure in a range of from about 200 MPa to about 250 MPa for a time period of from about 2 hours to about 3 hours. In some embodiments, the viral composition is subjected to a pressure in a range of from about 250 MPa to about 300 MPa for a time period of from about 30 minutes to about 2 hours, or from about 30 minutes to about 60 minutes. In some embodiments, the viral composition is subjected to a pressure in a range of from about 300 MPa to about 350 MPa for a time period of from about 30 minutes to about 60 minutes, or from about 15 minutes to about 60 minutes, or from about 15 minutes to about 45 minutes, or from about 15 minutes to about 30 minutes. In some embodiments, the viral composition is subjected to a pressure in a range of from about 350 MPa to about 400 MPa for a time period of from about 1 minute to about 60 minutes, or from about 1 minute to about 30 minutes, or from about 1 minute to about 15 minutes, or from about 10 minutes to about 15 minutes, or from about 5 minutes to about 30 minutes, or from about 10 minutes to about 30 minutes, or from about 15 minutes to about 30 minutes.

An external pressure source is used for supplying pressure to the pressure chamber of the vessel containing the viral composition. According to Pascal's Law, this hydrostatic pressure has a uniform effect on all materials inside the pressure vessel. Any known device that provides for a pressure of up to about 500 MPa or greater (e.g., up to about 1000 MPa) is suitable for use in carrying out a subject method. See, e.g., Cléry-Barraud et al. (2004) Appl Environ Microbiol. 70(1): 635-637; and high hydrostatic pressure systems available from Avure Technologies (Kent, Wash.).

A viral composition comprises an AAV (e.g., an AAV particle, an rAAV particle), and a non-AAV virus (e.g., a non-AAV viral particle). In many embodiments, a viral composition is a cell-free viral composition. The viral composition is generally free of cellular proteins and/or other contaminants. A viral composition may comprise one or more additional components, where such components may be one or more of: a buffer (e.g., a phosphate buffer, a Tris buffer, etc.); a salt (e.g., NaCl, $MgCl_2$, etc.); ions, e.g., magnesium ions, manganese ions, zinc ions, etc.); a preservative; a solubilizing agent; a detergent, e.g., a non-ionic detergent; dimethylsulfoxide; and the like.

In some embodiments, the viral composition is a crude lysate, e.g. a cell lysate. In some embodiments, one or more ion exchange chromatographic procedures are carried out before or after a subject hydrostatic pressure treatment. See, e.g., U.S. Pat. No. 6,566,118. For example, opposing ion exchange chromatography steps may be applied in any order, and may include additional opposing ion exchange chromatography step(s). For example, in some embodiments, a lysate or culture supernatant is subjected to cation exchange chromatography followed by anion exchange chromatography followed by cation exchange chromatography. In some embodiments, heparin sulfate is used in at least one (e.g., the last) cation exchange chromatography step.

For example, a clarified AAV lysate can be loaded on an positively charged anion-exchange column, such as an N-charged amino or imino resin (e.g. POROS 50 PI, or any DEAE, TMAE, tertiary or quaternary amine, or PEI-based resin) or a negatively charged cation-exchange column (such as HS, SP, CM or any sulfo-, phospho- or carboxy-based cationic resin). The column can be washed with a buffer (such as chromatography buffer A/TMEG). The column can be eluted with a gradient of increasing NaCl concentration and fractions can be collected and assayed for the presence of AAV and/or contaminants.

Other procedures can be used in place of, or in addition to, the above-described anion and cation exchange procedures, based on inter-molecular associations mediated by features other than charge as is known in the art. Such other procedures include intermolecular associations based on ligand-receptor pairs (such as antibody-antigen or lectin-carbohydrate interactions), as well as separations based on other attributes of the molecules, such as molecular sieving chromatography based on size and/or shape. As one non-limiting example, the filtrate or partially purified AAV preparation may be loaded on a column that contains an AAV-specific antibody. This column can bind AAV. The column can be rinsed with buffer to remove contaminating proteins, and then eluted with a gradient or step of increasing NaCl concentration and fractions can be collected. Alternatively, such a column can be eluted with a buffer of different pH than that of the loading buffer.

The peaks of AAV and adenovirus can be identified in the fractions by infectivity assays or by a nucleic acid hybridization assay or an immunoassay. The peaks can be pooled, and the pool can be diluted or dialyzed or diafiltered with a buffer (e.g. TMEG or equivalent) to reduce the salt concentration.

This pool can be injected on a positively charged anion-exchange column and/or a negatively charged cation-exchange column (such as those referred to above). The column can be washed with a buffer (such as chromatography buffer A/TMEG). The column can be eluted with a gradient of increasing NaCl concentration and fractions can be collected. The peaks of AAV and adenovirus can be identified in the fractions by an infectivity assay or by a nucleic acid hybridization or immunoassay. The peaks can be pooled based on the results of any of these assays.

The pool of AAV-containing fractions eluted from an anion exchange column as described above can be concentrated and purified by tangential flow filtration (TFF), for example in a Filtron Ultrasette or Millipore Pellicon unit. A membrane of suitable molecular weight cut-off (such as a 100,000 or 300,000 cut-off), is typically composed of a polymer such as regenerated cellulose or polyethersulfone. The preparation is filtered through the membrane, and the product is retained. The retained material can be diafiltered using the membrane with successive washes of a suitable buffer such as Ringer's Balanced Salt Solution +5% glycerol. The final sample is highly enriched for the product and can be sterile filtered through a 0.2µ filter and stored for use.

In the purification and concentration of AAV with tangential flow filtration from post-anionic exchange column material, the 300,000 molecular weight cut-off membrane has resulted in higher yields of replicative units than the 100,000 molecular weight cut-off membrane.

An additional step that can be employed for removal of adenovirus, if desired, involves treating the eluant pool with a heat inactivation step (as described herein) and then filtration (e.g. prior to subjecting the preparation to TFF).

In some embodiments, lysate or culture supernatant is subjected to filtration (such as depth filtration) to clarify the lysate, followed by heat killing, followed by filtration (such as filtration using a 0.5 µm filter) to further clarify the lysate, followed by cation exchange chromatography (using, for example, an HS resin), followed by nuclease digestion, followed by anion exchange chromatography (using, for example, a PI resin), followed by heparin sulfate chromatography, followed by gel filtration.

Compositions

The present invention further provides a viral composition, including a pharmaceutical composition, which is produced using a subject method, where the viral composition comprises active AAV and inactivated non-AAV. A subject viral composition is in some embodiments a helper virus-free composition. A subject viral composition will in some embodiments comprise active AAV (e.g., active AAV particles, active rAAV particles), and inactivated non-AAV virus; and will in some embodiments include one or more of: a buffer (e.g., a phosphate buffer, a Tris buffer, etc.); a salt (e.g., NaCl, $MgCl_2$, etc.); ions, e.g., magnesium ions, manganese ions, zinc ions, etc.); a preservative; a solubilizing agent; a detergent, e.g., a non-ionic detergent; dimethylsulfoxide; and the like. In some embodiments, a subject composition, including a subject pharmaceutical composition, will comprise an amount of from about $10^6$ to about $10^{15}$ of the rAAV virions, e.g., from about $10^8$ to $10^{12}$ rAAV virions per unit dosage form, e.g., per ml, per 0.5 ml, etc.

In some embodiments, a subject viral composition is a pharmaceutical composition, comprising a pharmaceutically acceptable excipient. In some instances, the composition can comprise a pharmaceutically acceptable excipient, a variety of which are known in the art and need not be discussed in detail herein. Pharmaceutically acceptable excipients have been amply described in a variety of publications, including, for example, "Remington: The Science and Practice of Pharmacy", 19$^{th}$ Ed. (1995) Mack Publishing Co.; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Selective Inactivation of Adenovirus in Mixed Viral Populations

It was discovered that AAV can be exposed to up to 300 MPa for at least 2 hours without experiencing any appreciable loss of infectivity. Furthermore, it was found that AAV can be exposed to 450 MPa for at least 15 minutes without a significant loss of infectivity. However, it was also found that at pressures of 500 MPa or greater, AAV begins to become inactivated even during a 15 minute incubation, and the degree of inactivation increases with the time over which the virus is exposed to elevated pressures. Therefore, these upper limits of AAV stability identify a regime of pressures and incubation times that can be used to selectively inactivate adenovirus while leaving AAV intact.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for selectively inactivating a helper virus in a cell-free viral liquid composition comprising adeno-associated virus (AAV) and the helper virus, the method comprising subjecting the composition to a hydrostatic pressure at a pressure in a range of from about 200 MPa to about 400 MPa and for a time such that at least about 50% of the helper virus is selectively inactivated, and wherein said AAV retains at least about 80% infectivity.

2. The method of claim 1, wherein the time is from about 1 minute to about 3 hours.

3. The method of claim 1, wherein the time is from about one hour to about 2 hours.

4. The method of claim 1, wherein the time is from about 1 minute to about 30 minutes.

5. The method of claim 1, wherein the composition is maintained at a temperature of less than about 40° C.

6. The method of claim 1, wherein the composition is maintained at a temperature of less than about 37° C.

7. The method of claim 1, wherein the composition is maintained at a temperature of less than about 35° C.

8. The method of claim 1, wherein the helper virus is an adenovirus.

9. The method of claim 1, wherein at least about 90% of the helper virus is inactivated.

10. The method of claim 1, wherein at least about 98% the helper virus is inactivated.

11. The method of claim 1, wherein the AAV is AAV serotype 2.

12. The method of claim 1, wherein the AAV is recombinant AAV.

13. The method of claim 1, wherein the AAV retains at least about 90% infectivity following subjecting the composition to hydrostatic pressure.

14. The method of claim 1, further comprising subjecting the liquid composition to one or more ion exchange chromatographic steps.

15. The method of claim 14, wherein the one or more ion exchange chromatographic steps comprise anion exchange chromatography.

16. The method of claim 14, wherein the one or more ion exchange chromatographic steps comprise cation exchange chromatography.

17. The method of claim 1, wherein the helper virus is a herpesvirus.

18. The method of claim 1, wherein the composition is maintained at a temperature of from about 4° C. to about 40° C.

19. The method of claim 1, wherein the helper virus is a vaccinia virus.

* * * * *

UNITED STATES PATENT AND TRADEMARK OFFICE
CERTIFICATE OF CORRECTION

PATENT NO. : 7,625,570 B1 Page 1 of 1
APPLICATION NO. : 11/372552
DATED : December 1, 2009
INVENTOR(S) : David V. Schaffer It is certified that error appears in the above-identified patent and that said Letters Patent is hereby corrected as shown below:

Column 1, line 14, insert the following revised statement:

GOVERNMENT RIGHTS

-- This invention was made with government support under grant number EB003007 awarded by the National Institutes of Health. The government has certain rights in this invention. --

Signed and Sealed this

Nineteenth Day of January, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,625,570 B1 | Page 1 of 1 |
| APPLICATION NO. | : 11/372552 | |
| DATED | : December 1, 2009 | |
| INVENTOR(S) | : Schaffer et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 130 days.

Signed and Sealed this

Twenty-third Day of November, 2010

David J. Kappos
*Director of the United States Patent and Trademark Office*